(12) United States Patent
    Allessie

(10) Patent No.: US 10,893,980 B2
(45) Date of Patent: Jan. 19, 2021

(54) ATTACHMENT FOR SWIMMING GOGGLES

(71) Applicant: Joseph J. Allessie, Ringwood, NJ (US)

(72) Inventor: Joseph J. Allessie, Ringwood, NJ (US)

( * ) Notice: Subject to any disclaimer, the term of this patent is extended or adjusted under 35 U.S.C. 154(b) by 11 days.

(21) Appl. No.: 15/960,295

(22) Filed: Apr. 23, 2018

(65) Prior Publication Data

US 2018/0303671 A1    Oct. 25, 2018

Related U.S. Application Data

(63) Continuation-in-part of application No. 12/261,904, filed on Oct. 30, 2008, now abandoned.

(60) Provisional application No. 60/983,686, filed on Oct. 30, 2007.

(51) Int. Cl.
    *A61F 9/00*     (2006.01)
    *A61F 9/02*     (2006.01)
    *G02C 3/00*     (2006.01)
    *A63B 33/00*    (2006.01)

(52) U.S. Cl.
    CPC .............. *A61F 9/027* (2013.01); *G02C 3/00* (2013.01); *A63B 33/00* (2013.01)

(58) Field of Classification Search
    CPC ............ A61F 9/027; G02C 3/00; A63B 33/00
    USPC .......................................................... 206/5
    See application file for complete search history.

(56) References Cited

U.S. PATENT DOCUMENTS

| | | | | |
|---|---|---|---|---|
| 1,715,348 A * | 6/1929 | Barbara | ............... | A45C 11/329 150/900 |
| 4,290,522 A * | 9/1981 | Takasaki | ................ | A45C 11/04 206/233 |
| 4,984,682 A * | 1/1991 | Cummins | ............... | A45C 11/04 206/5 |
| 5,032,019 A * | 7/1991 | Burchett | ................ | A45C 11/04 206/5 |
| 5,526,924 A * | 6/1996 | Klutznick | .............. | A45C 11/04 206/5 |
| 5,833,053 A * | 11/1998 | Wood | ...................... | A45C 11/04 206/5 |
| 6,799,707 B2 * | 10/2004 | Gibson | ................. | A63C 11/006 224/607 |
| 7,014,042 B2 * | 3/2006 | Lane | ...................... | A45C 11/04 206/467 |
| 2010/0071118 A1 * | 3/2010 | Tobey | .................. | A63B 33/002 2/452 |
| 2011/0318512 A1 * | 12/2011 | Tobey | .................. | A63B 33/002 428/34.1 |

* cited by examiner

*Primary Examiner* — Khaled Annis
(74) *Attorney, Agent, or Firm* — West & Associates, A PC; Stuart J. West; Charlotte Rodeen-Dickert

(57) ABSTRACT

A sporting-goods device capable of removably attaching to eyewear, specifically swimming goggles, and another object to prevent loss of the eyewear.

14 Claims, 9 Drawing Sheets

ATTACHMENT FOR SWIMMING GOGGLES

CLAIM OF PRIORITY

This application is a continuation-in-part application of prior-filed and co-pending U.S. patent application Ser. No. 12/261,904, filed Oct. 30, 2008, which claims priority under 35 U.S.C. § 119(e) from earlier filed U.S. Provisional Application Ser. No. 60/983,686, filed Oct. 30, 2007, by Joseph Allessie, the entireties of each of which are hereby incorporated herein by reference.

BACKGROUND

Field of the Invention

The present disclosure relates to the field of sporting goods, specifically an accessory to prevent loss of swimming goggles.

Background

Recreational and professional swimmers alike use swimming goggles to both protect their eyes from chlorinated water and to be able to see clearly under water. However, many swimmers often find themselves in need of a new pair because they mistakenly leave their goggles on the edge of the pool, on a lounge chair, in a locker room, or because they sink and cannot be located.

Replacing lost goggles can be expensive, especially with children who are notorious for losing goggles, for professional swimmers who often buy high-end, high-priced goggles, or for swimmers who buy custom corrective lens goggles. It is therefore important to have a lightweight goggle accessory that can removably attach to both a pair of goggles and another object, such as an arm, a pool bag, or a keychain. It is also important to keep goggles afloat to prevent sinking. This type of device would keep a swimmer's goggles either on his or her body or together with other personal items when not in use, thereby decreasing the chance of loss or inadvertent damage. This type of device could be used with other kinds of eyewear, such as sunglasses or reading glasses, to prevent loss of those items as well.

Eyeglass retention devices currently exist on the market, such as those sold by Croakies®, but those devices are not suitable for use with goggles. Additionally, although a goggle retaining device is described in U.S. Pat. No. 5,987,650, that device is for attachment of goggles to a swimsuit, is not removable from the swimsuit, and therefore cannot be used with other objects, such as a tote bag.

What is needed is a lightweight device that can removably attach to both a pair of goggles or other eyewear and the owner's body or another object to prevent loss.

DETAILED DESCRIPTION

Figure 1:
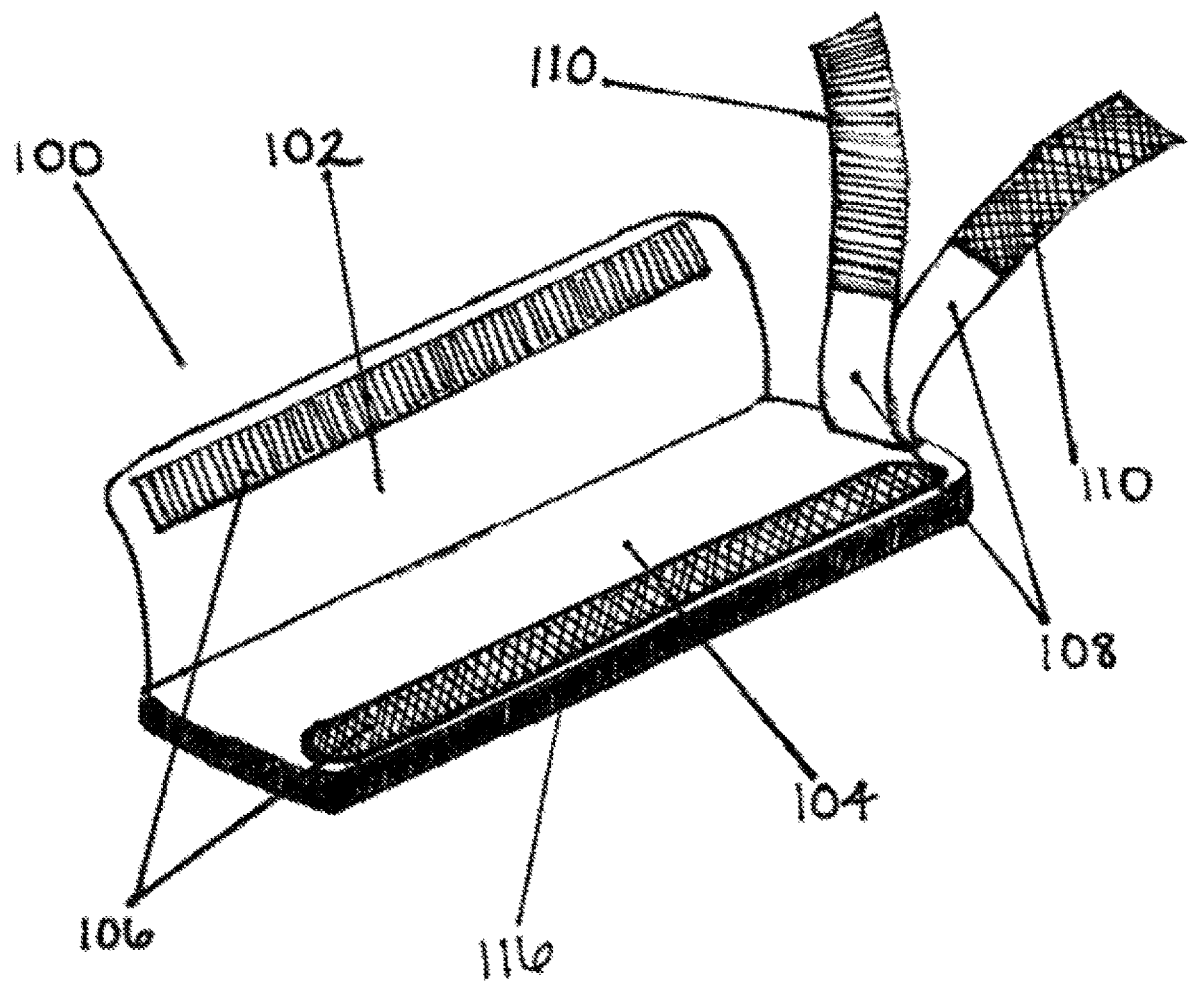
FIG. 1 depicts a perspective view of an embodiment of the present device.

FIG. 1 shows a perspective view of an embodiment of the present device 100. At least one edge of the lower surface of a first substantially planar member 102 can be connected to at least one edge of the upper surface of a second substantially planar member 104. The lower surface of said first substantially planar member 102 and the upper surface of said second substantially planar member 104 can each be connected to at least one fastening region 106. Said fastening regions 106 can be paired to mate with each other, such that said first and second substantially planar members 102 and 104 can removably attach to each other. Fastening regions 106 can be in the form of strips covering a small portion of each of said first and second substantially planar members 102 and 104, as shown in FIGS. 1-1C, or can cover the entire surface area of at least one of said first and second substantially planar members 102 and 104.

Figure 1A:
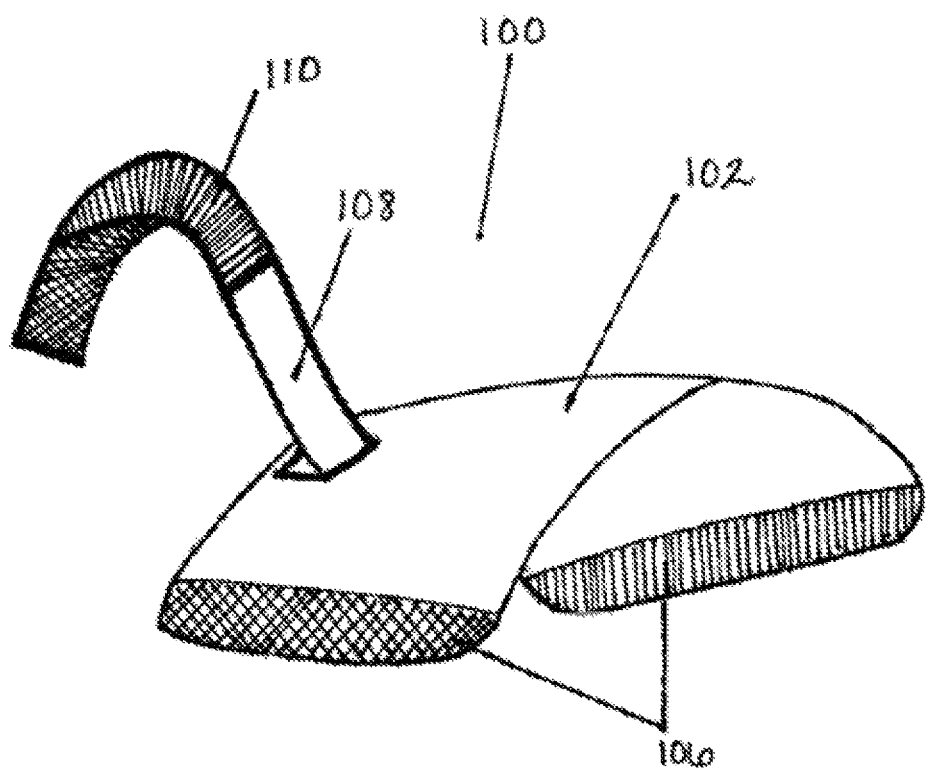
FIG. 1A depicts a perspective view of another embodiment of the present device.
Figure 1B:
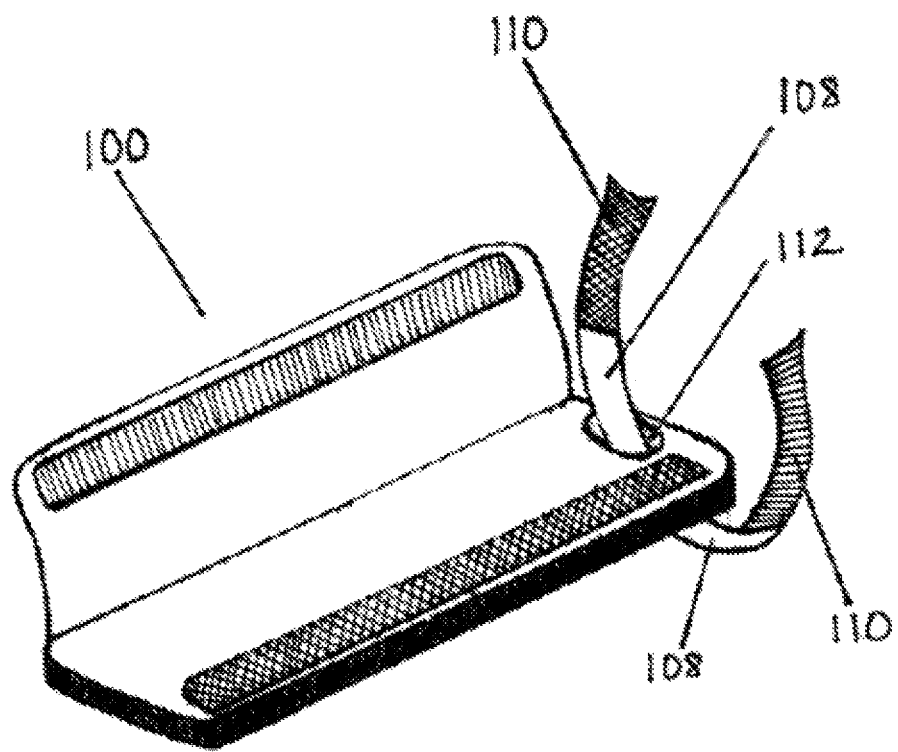
FIG. 1B depicts a perspective view of yet another embodiment of the present device.

At least one of said first and second substantially planar members 102 and 104 can be coupled with at least one elongated flexible member 108. In FIG. 1, elongated flexible members 108 are connected substantially close to a short edge of a second substantially planar member 104. In another embodiment, as shown in FIG. 1B, a second substantially planar member 104 can have an aperture 112 adapted to accept at least one elongated flexible member 108. In alternate embodiments, at least one elongated flexible member 108 can be coupled with any other known and/or convenient location on or through at least one of said first or second substantially planar members 102 and 104.

Figure 1C:
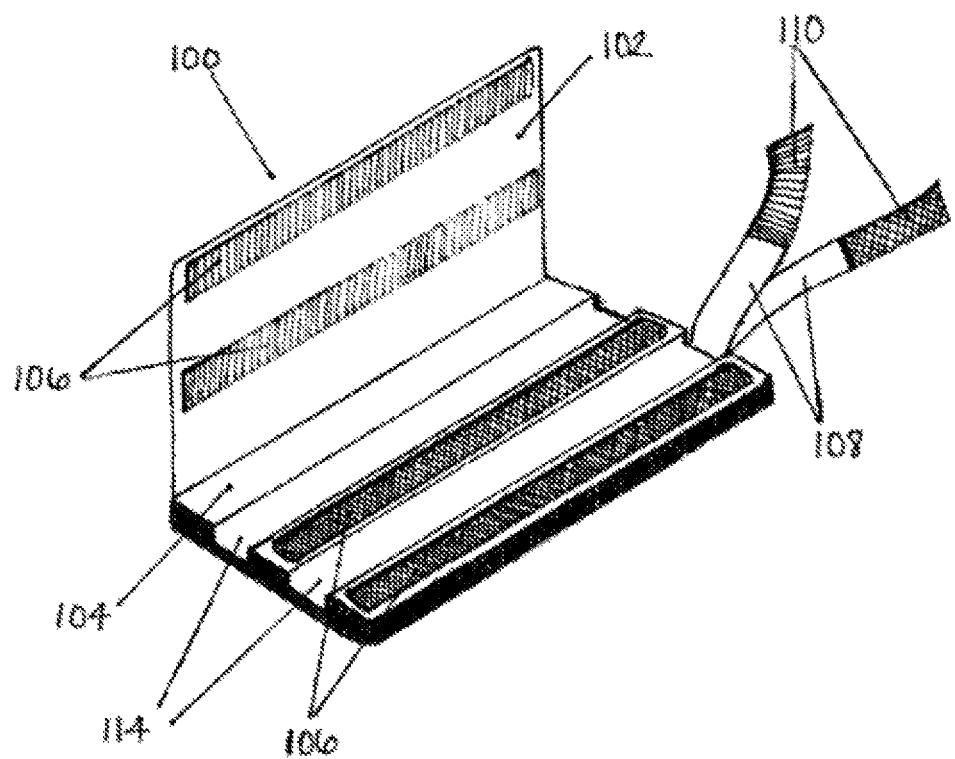
FIG. 1C depicts a perspective view of yet another embodiment of the present device.
Figure 2:
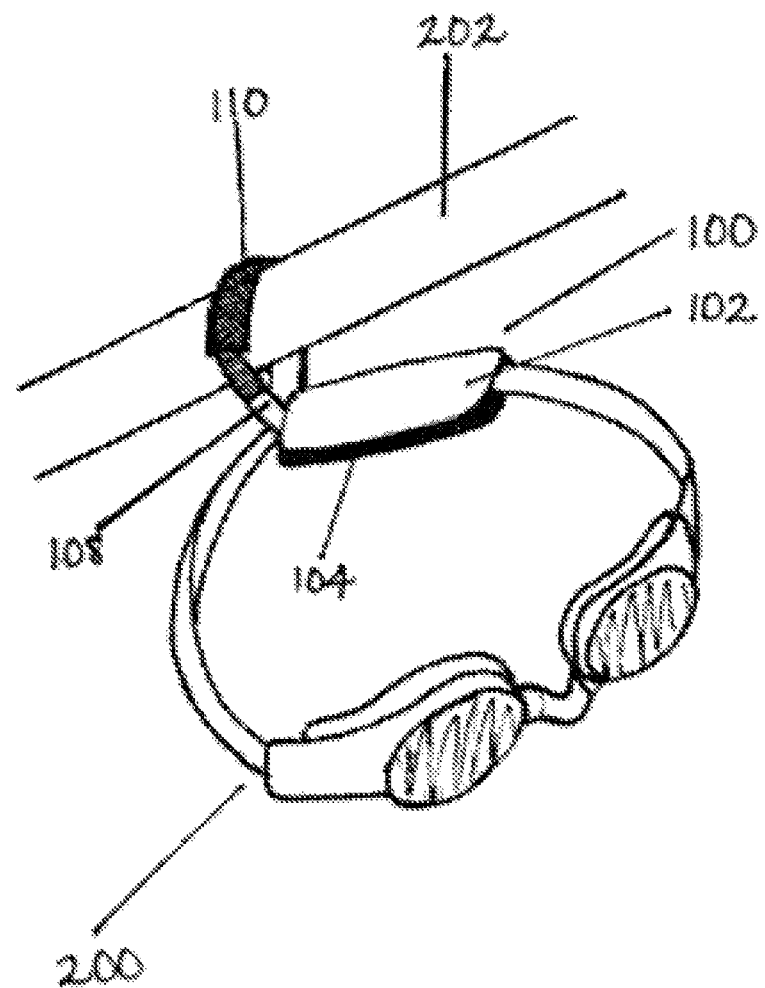
FIG. 2 depicts a perspective view of an embodiment of the present device in an in-use configuration.

As shown in FIG. 1C, at least one of said first and second substantially planar members 102 and 104 can have at least one channel 114 running through it adapted to accommodate the strap of a pair of goggles and/or at least one elongated flexible member 108 and temporarily secure said strap and/or elongated flexible member 108 when substantially planar members 102 and 104 are removably attached to each other via said fastening regions 106 (see FIG. 2). FIG. 1C shows a device 100 comprising two channels 114 and two sets of fastening regions 106 on the surfaces of substantially planar members 102 and 104, such that a user can selectively cover or expose one or both channels 114 with a first substantially planar member 102. In this embodiment, a user can keep the strap of a pair of goggles secured within device 100 while selectively exposing at least one elongated flexible member 108. In other embodiments, a single channel 114 can be adapted to accommodate both a goggle strap and at least one elongated flexible member 108 at the same time.

At least one side of said elongated flexible member 108 can be coupled with at least one set of complementary fastening components 110. As shown in FIG. 1, two elongated flexible members 108 can be coupled with a set of complementary fastening components 110 such that said elongated flexible members 108 can removably attach to each other. As shown in FIG. 1A, in another embodiment device 100 can have one elongated flexible member 108, both sides of which can be coupled with a set of complementary fastening components 110 such that the ends of said elongated flexible member 108 can removably attach to each other.

FIG. 1 shows said fastening regions 106 as being connected to said first and second substantially planar members 102 and 104 along an edge opposite the edge where the substantially planar members 102 and 104 are connected to each other. In an alternate embodiment, at least one fastening region 106 can be integral with the material of at least one of said first and second substantially planar members 102 and 104. In other embodiments said fastening regions 106 can be connected at any other known and/or convenient location on said first and second substantially planar members 102 and 104.

As shown in FIG. 1A, an alternate embodiment of the device 100 can have just one substantially planar member 102 having an upper surface and a lower surface. Said substantially planar member 102 can connected to at least one fastening region 106, such that one edge of the upper surface of a substantially planar member 102 can removably attach to the opposite edge of the lower surface of a substantially planar member 102. In some embodiments, at least two edges of each of the upper and lower surfaces of a substantially planar member 102 can be connected to fastening regions 106, such that opposite edges of the same surface can also removably attach to each other.

In FIG. 1, said first and second substantially planar members 102 and 104 are rectangular. In alternate embodiments, said first and second substantially planar members 102 and 104 can have any other known and/or convenient geometry. In FIG. 1, the first and second substantially planar members 102 and 104 are made of neoprene. In alternate embodiments, at least one of said first and second substantially planar members 102 and 104 can be made of any other known and/or convenient buoyant material, such that the entire device 100 can float in a body of water and can keep afloat a pair of goggles. In other embodiments, at least one of said first and second substantially planar members 102 and 104 can be made of or can be connected to an inflatable bladder 116, whereby a user can selectively inflate the bladder 116 by blowing air into it, thereby making the device 100 buoyant. Said inflatable bladder 116 can be a single cell or can be comprised of a plurality of cells that inflate simultaneously. In yet other embodiments, said bladder 116 can be pre-filled either wholly or partially with a water-buoyant gas or liquid and sealed.

Said fastening regions 106 and set of complementary fastening components 110 can be hook and loop, snaps, protrusion and aperture, or any other known and/or convenient fastening mechanisms. At least one of said first and second substantially planar members 102 and 104 can be connected to a piece of fluorescent material such that the device 100 can be easily spotted from a distance or in the dark. In alternate embodiments, at least one of said first and second substantially planar members 102 and 104 can be made of or integral with a piece of fluorescent material. A first substantially planar member 102 can also be a different color than a second substantially planar member 104. In use, each device 100 of a set of devices 100 can have distinguishing colors and/or markings such that users can identify which device 100 belongs to each owner or each pair of goggles.

Referring to FIG. 2, in use a user wraps first and second substantially planar members 102 and 104 around a strap of a pair of goggles 200. A user can then removably attach one edge of the lower surface of a first substantially planar member 102 to the upper surface of a second substantially planar member 104 via fastening regions 106. At this stage, the device 100 can be removably attached to the strap of a pair of goggles 200. A user can then wrap elongated flexible members 108 around a convenient object 202, as shown in FIG. 2, or a part of the user's body. A user can then removably attach said elongated flexible members 108 to each other via a set of complementary fastening components 110, such that the device 100 is removably attached to both a pair of goggles 200 and a convenient object 202.

Alternatively, a user can tuck elongated flexible members 108 inside said first and second substantially planar members 102 and 104 while said substantially planar members 102 and 104 are wrapped around the strap of a pair of goggles 200. In this manner, a user does not have to attach the elongated flexible members 108 to a convenient object 202. Although a pair of goggles 200 would not be attached to a convenient object 202, the device 100 could still keep a pair of goggles 200 afloat if they became separated from a user and landed in a body of water.

Figure 3:
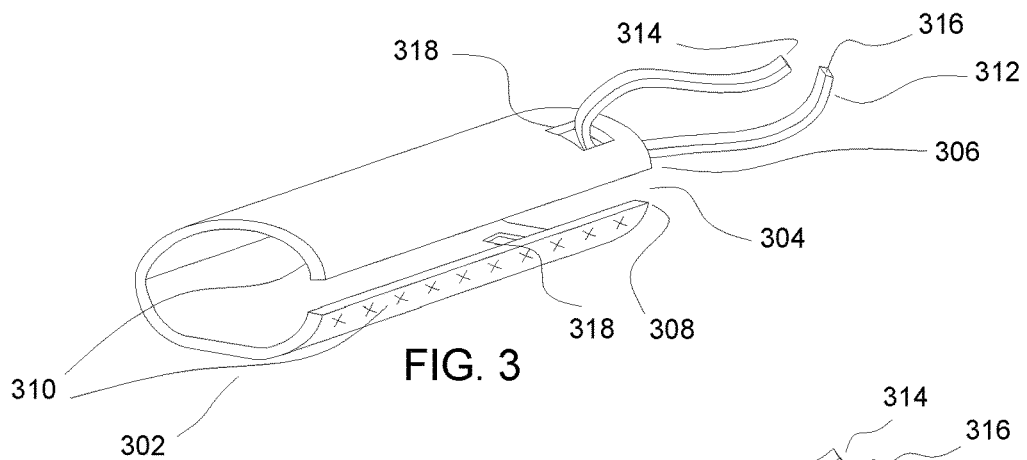
FIG. 3 depicts a perspective view of another embodiment of the present device.

FIG. 3 shows a perspective view of an embodiment of the present device 300. A flexible, open-ended, substantially tubular member 302 can have at least one longitudinal seam 304 with a first edge 306 and a second edge 308. As shown in FIG. 3, some embodiments can have corresponding fastening regions 310 located on the inner surface of a first edge 306 and the outer surface of a second edge 308, or the outer surface of a first edge 306 and the inner surface of a second edge 308. In such embodiments, a first edge 306 and a second edge 308 can be removably connected longitudinally by hook-and-loop closures, snaps, clips, magnets, or any other known and/or convenient device. In other embodiments having more than one longitudinal seam 304, a first edge 306 and a second edge 308 can be removably attached via stitching, adhesive, or any other known and/or convenient method.

In some embodiments, a flexible, substantially tubular member 302 can be comprised of a closed-cell foam, polymer, neoprene, or any other known and/or convenient material having buoyant properties. In alternate embodiments, a flexible, substantially tubular member 302 can comprise a fluorescent or phosphorescent exterior. In some embodiments, a flexible, substantially tubular member 302 can comprise at least two layers, such that the space between layers can be filled with air, gel, or any other buoyant material. In alternate embodiments, a flexible, substantially tubular member 302 can have a slightly weighted region such that a device 300 can orient itself in a desired position when floating in water. In other embodiments, the exterior surface of a flexible, substantially tubular member 312 can be textured, smooth, or any other known and/or convenient surface finish. As shown in FIG. 3, a flexible, substantially tubular member 302 can be configured to have an inner diameter dimensioned to accommodate a single or double swimming goggle strap and a length less than that of a swimming goggle strap, but in other embodiments can have any other known and/or convenient dimensions.

A flexible substantially tubular member 302 can be coupled with at least one elongated flexible member 312. In some embodiments, an elongated flexible member 312 can have a first end 314 and a second end 316. As shown in FIG. 3, some embodiments, a first end 314 and a second end 316 can be removably connected to form a closed loop by selectively engaging hook-and-loop closures, snaps, clips, magnets, or any other known and/or convenient device. In some embodiments a elongated flexible member 312 can have a cross-sectional geometry such that a first end 314 and a second end 316 can removably connect substantially longitudinally end-to-end to form a closed loop. In other embodiments, an elongated flexible member 312 can have a substantially planar geometry such that a first end 314 and a second end 316 can connect in an overlapping configuration to form a closed loop. In some embodiments, an elongated flexible member 312 can have a textured surface, but in other embodiments, can be substantially smooth or any other known and/or convenient surface finish.

In FIG. 3, an elongated flexible member 312 can be connected proximal to an open end of a substantially tubular member 302. In some embodiments, as shown in FIG. 3, a flexible substantially tubular member 302 can have at least one aperture 318 through which an elongated flexible member 312 can pass and attach to a flexible substantially tubular member 302. In some embodiments, an elongated flexible member 312 can have at least one thicker region or knot located along its length to limit longitudinal motion of a flexible elongated member 312 through an aperture 318. In other embodiments, at aperture 318 can be dimensioned to selectively engage with a flexible elongated member 312 via a friction fit connection to limit longitudinal motion of a flexible elongated member. In alternate embodiments there can be more than one aperture 318. In other embodiments, an elongated flexible member can be coupled with any other known and/or convenient location on or through a side of a flexible, substantially tubular member 302.

In other embodiments, an elongated flexible member 312 can be a closed loop having one end that can be threaded through at least one aperture 318 and the other end threaded through the emerging opposite end to removably connect an elongated flexible member 312 to a flexible substantially tubular member 302.

Figure 4:
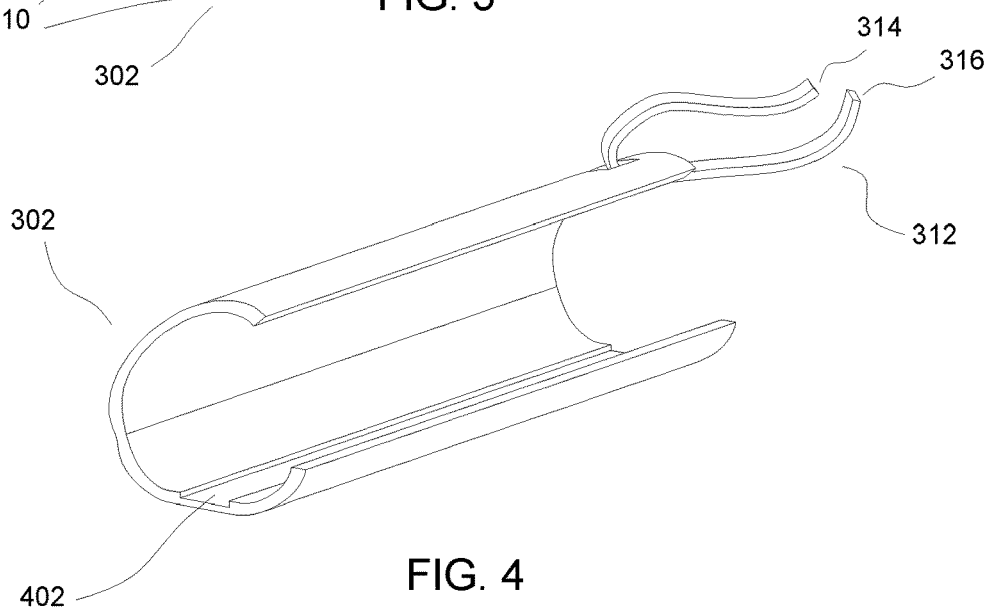
FIG. 4 depicts a perspective view of yet another embodiment of the present device.

FIG. 4 depicts another embodiment of the present device. In FIG. 4, the interior surface of a flexible, substantially tubular member 302 can have at least one depressed longitudinal region 402. As shown in FIG. 4, a depressed longitudinal region 402 can extend substantially the length of a flexible, substantially tubular member 302. In some embodiments, a depressed longitudinal region 402 can be configured to accommodate at least one swimming goggle strap, but in other embodiments can be any other known and/or convenient dimension. In alternate embodiments, an adhesive or any other known and/or convenient gripping device can cover at least a portion of the surface area of a depressed longitudinal region 402. In still other embodiments, an adhesive or any other known and/or convenient gripping device can cover at least a portion of the interior surface of a flexible, substantially tubular member 302.

Figure 5:
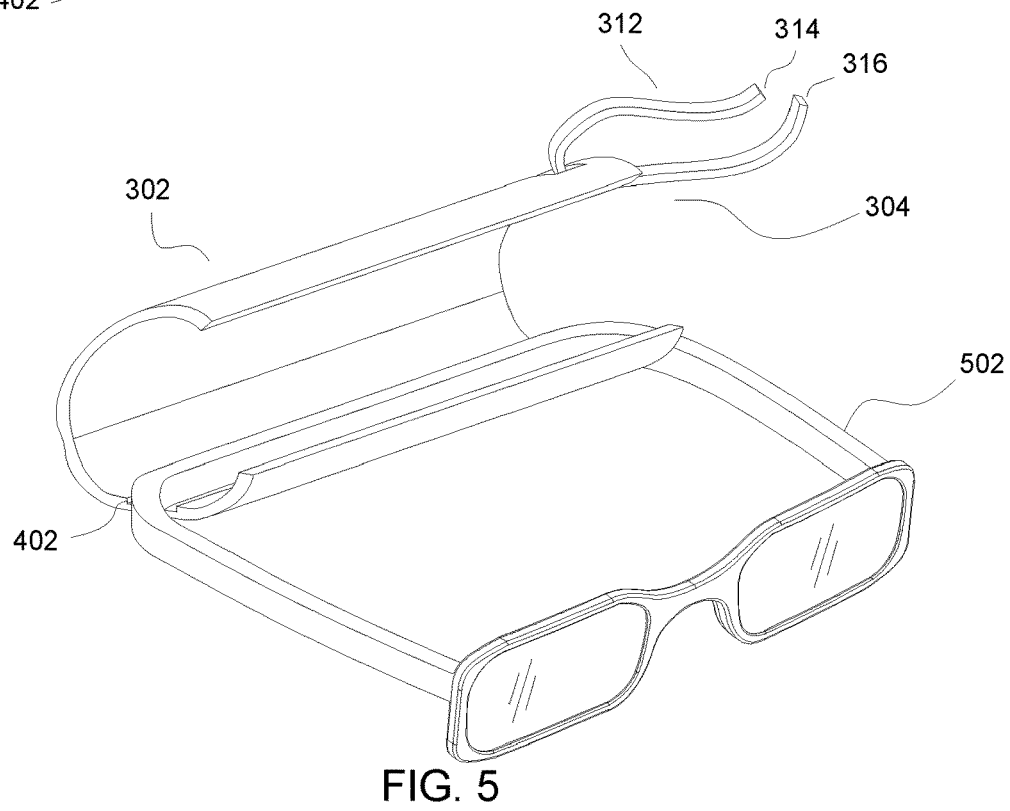
FIG. 5 depicts a perspective view of yet another embodiment of the present device.

In use, as shown in FIG. 5, a user can open a flexible, substantially tubular member 302 along a longitudinal seam 304 and place it around a swimming goggle strap 502. In embodiments having a depressed longitudinal region 402, a user can position a substantially tubular member 302 such that at least one swimming goggle strap 502 can be substantially aligned with and rest in a depressed longitudinal region 402. A user can then close and attach a longitudinal seam 304 such that a substantially tubular member 302 can encircle a swim goggle strap.

Figure 6:
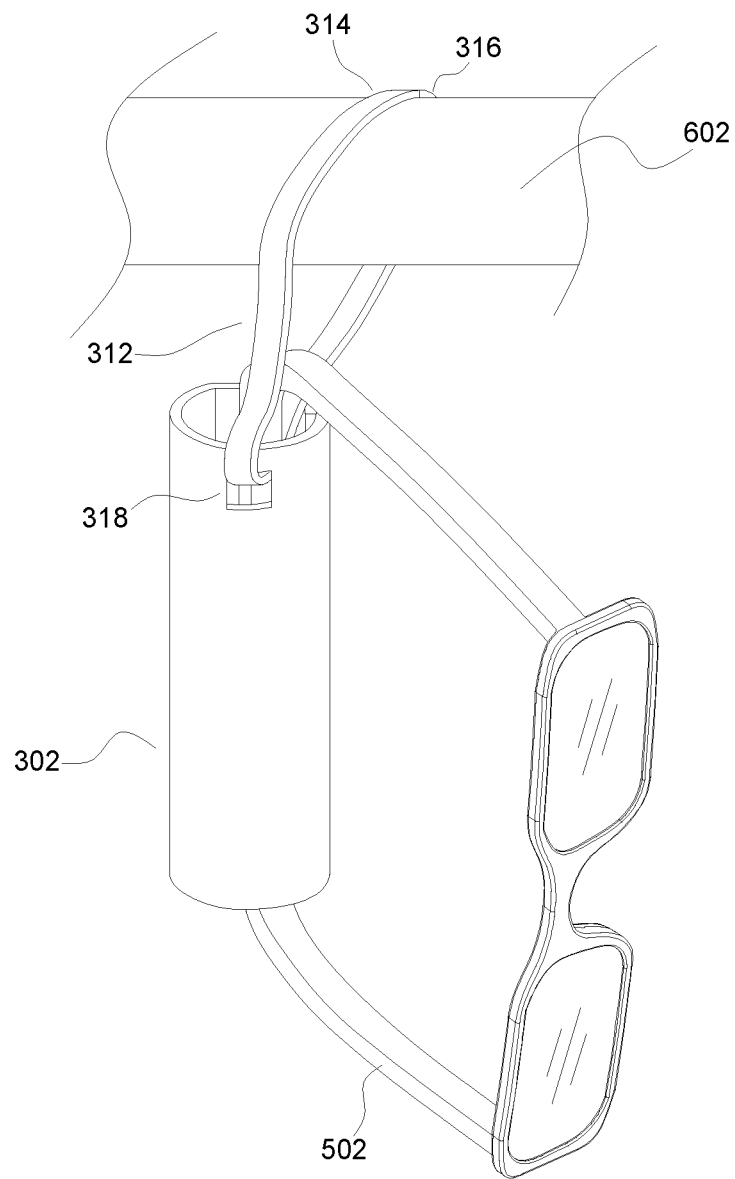
FIG. 6 depicts a perspective view of another embodiment of the present device in an in-use configuration.

As shown in FIG. 6, a user can then separate said first end 314 and said second end 316 of an elongated flexible member 312 to position an elongated flexible member 312 around a convenient object 602, such as, but not limited to, a bag strap, belt, rail, or a part of the user's body, such as a wrist. A user can then removably connect a first end 314 and second end 316 of an elongated flexible member 312 to each other such that the device 300 can be removably attached to both a pair of goggles and a convenient object. In other embodiments, such as those in which an elongated flexible member 312 is a substantially closed loop, a user can loop said elongated flexible member 312 around a convenient object 602 and pass a flexible substantially tubular member 302 containing a goggle strap 502 through the looped end to secure the device 300 to a convenient object.

A user can also tuck an elongated flexible member 312 inside said flexible, substantially tubular member 302 that is wrapped around the strap of a pair of goggles. In this manner, a user does not have to attach an elongated flexible member 312 to a convenient object. Although a pair of goggles would not be attached to a convenient object, the device 300 could still keep a pair of goggles afloat if they became separated from a user and landed in a body of water.

Figure 7:
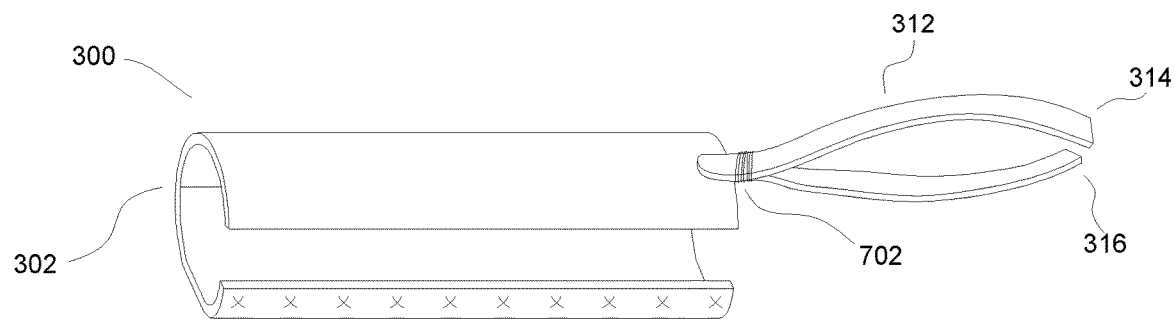
FIG. 7 depicts a perspective view of yet another embodiment of the present device.

FIG. 7 depicts another embodiment of the present device. In such embodiments, an elongated flexible member 312 can be attached to a flexible substantially tubular member 302 by a connecting device 702. As shown in FIG. 7, a connecting device 702 can be a swivel connector, but in other embodiments can be any other known and/or convenient device. A connecting device 702 can be located on the interior surface, exterior surface, or through a flexible substantially tubular member 302.

Figure 8:
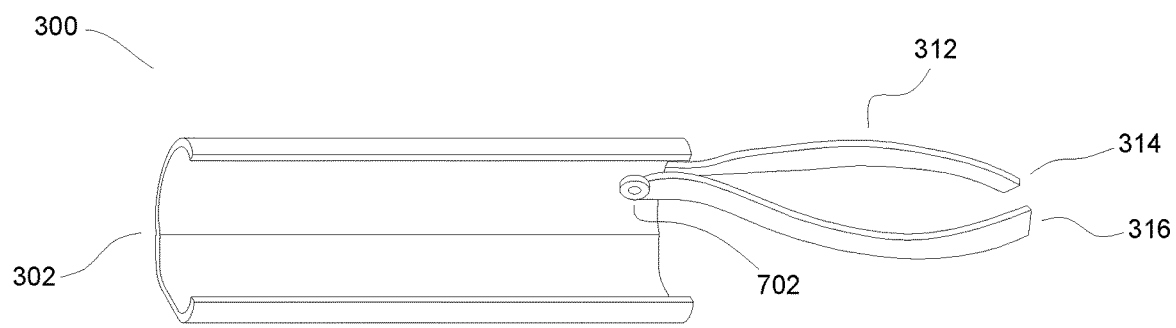
FIG. 8 depicts a perspective view of yet another embodiment of the present device.

FIG. 8 depicts another embodiment of the present device. In such embodiments, an elongated flexible member 312 can be attached to a flexible substantially tubular member 302 by a connecting device 702. As shown in FIG. 8, a connecting device 702 can also be a pivot connector, which can be oriented to allow a pivoting motion of an elongated flexible member 312 in a path substantially parallel to the end of a flexible substantially tubular member 302. In other embodiments, a pivot connector can be oriented to allow a pivoting motion of an elongated flexible member 312 in a path substantially perpendicular to the end of a flexible substantially tubular member 302. In still other embodiments, a pivot connector can be oriented to allow a pivoting motion of an elongated flexible member 312 in a path at any known and/or convenient angle relative to the end of a flexible substantially tubular member 302.

An elongated flexible member 312 can be divided into a first end 314 and a second end 316. In such embodiments, both a first end 314 and a second end 316 can be connected to a flexible substantially tubular member 302 on an interior surface via a connecting device 702. In other embodiments, both a first end 314 and a second end 316 can be connected to a flexible substantially tubular member 302 on an exterior surface. In other embodiments, as shown in FIG. 8, a first end 314 and a second end 316 of an elongated flexible member 312 can be connected to a flexible substantially tubular member 302 with a first end 314 proximal to an exterior surface of a flexible substantially tubular member 302 and a second end 316 proximal to an interior surface of a flexible substantially tubular member 302. A pivot connector can be a snap, button, hook, or any other known and/or convenient device. In such embodiments, an elongated flexible member 312 can be rotated such that it can extend substantially lengthwise along the interior surface of a flexible substantially tubular member 302.

Figure 9:
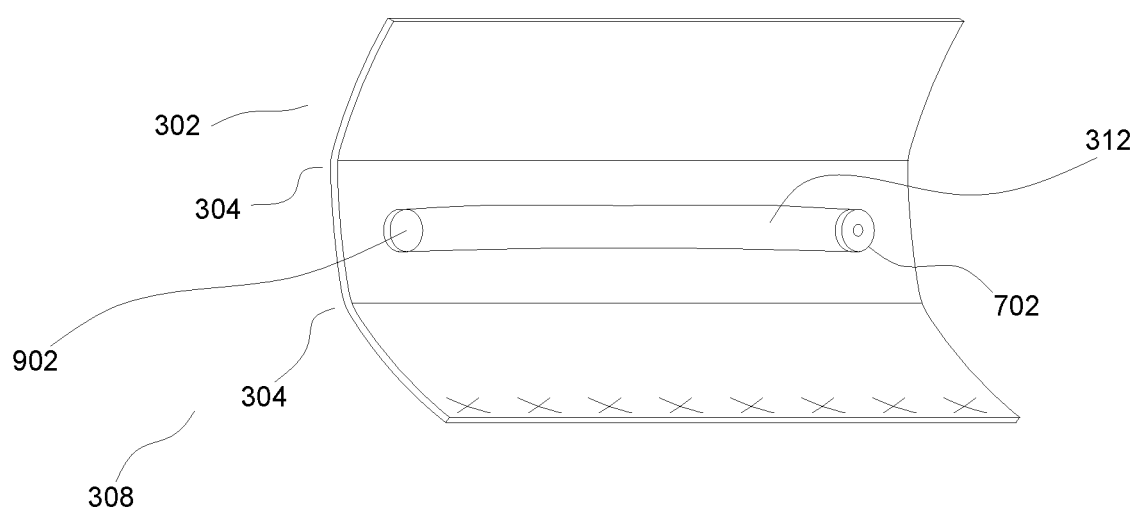
FIG. 9 depicts a perspective view of yet another embodiment of the present device.

FIG. 9 depicts another embodiment of the present device in which a flexible substantially tubular member 302 can have at multiple substantially longitudinal seams 304. In such embodiments, an elongated flexible member 312 can be connected at a point in a region delineated by two multiple substantially longitudinal seams 304. In such embodiments, an elongated flexible member 312 can be positioned proximal to the interior surface of a flexible substantially tubular member 302 when not deployed. In some embodiments an elongated flexible member 312 can be removably attached proximal to the opposite end of a flexible substantially tubular member 302 by a second connecting member 902, which can be a snap, button, or any other known and/or convenient device.

Although the invention has been described in conjunction with specific embodiments thereof, it is evident that many alternatives, modifications and variations will be apparent to those skilled in the art. Accordingly, the invention as described and hereinafter claimed is intended to embrace all such alternatives, modifications and variations that fall within the spirit and broad scope of the appended claims.

What is claimed is:

1. An eyewear retaining device, comprising:
a flexible, open-ended, substantially tubular member having an interior surface and an exterior surface of a wall, a first and second end, and at least one longitudinal seam with a first edge and a second edge,
   wherein said first edge and said second edge of said at least longitudinal seam are removably connected by a connecting device located on at least one surface of a said first edge and at least one surface of said second edge, and
   wherein said flexible, open-ended, substantially tubular member is comprised of a buoyant material;
an aperture through the wall of said flexible, open-ended, substantially tubular member proximal to an open end;
at least one elongated flexible member having a first end and a second end,
   wherein said elongated flexible member is passed through said aperture such that the first end is on a one side of the aperture and the second end is on an opposite side of the aperture and said first end and said second end are removably connected;
   and wherein said flexible, open-ended substantially tubular member selectively engages a flexible strap portion of a pair of swimming goggles having a set of lenses when said flexible strap portion is placed to the interior of said flexible, open-ended substantially tubular member and said first edge and said second edge of said at least one longitudinal seam are removably connected, said set of lenses is situated outside of said flexible, open-ended substantially tubular member at all times.

2. The device of claim 1, wherein the interior surface of said flexible, open-ended, substantially tubular member further comprises a narrow, depressed region dimensioned to accommodate the strap portion of the pair of goggles and/or said at least one elongated flexible member, running substantially longitudinally along at least a portion of a length of said flexible, open-ended, substantially tubular member.

3. The device of claim 2, wherein texturing covers at least a portion of the interior surface of the flexible, open-ended, substantially tubular member.

4. The device of claim 1, wherein said at least one elongated flexible member comprises a first elongated flexible member with a proximal end and a distal end, a second elongated flexible member with a proximal end and a distal such that the distal end of said first elongated flexible member removably couples to the distal end of said second elongated flexible member
   wherein the proximal end of said first elongated flexible member and the proximal end of said second elongated member are each removably coupled to said flexible, open-ended substantially tubular member.

5. The device of claim 4, further comprising a connecting member to removably couple said elongated flexible member and said flexible, open-ended tubular member.

6. The device of claim 4 wherein said connecting member is a swivel device.

7. The device of claim 4 wherein said connecting member is a pivoting device.

8. The device of claim 1, wherein said flexible, open-ended, substantially tubular member is made of buoyant material.

9. The device of claim 8, wherein said buoyant material is neoprene.

10. The device of claim 1, wherein said flexible, open-ended, substantially tubular member further comprises fluorescent properties.

11. The device of claim 1, wherein said flexible, open-ended, substantially tubular member further comprises phosphorescent properties.

12. The device of claim 1, wherein said flexible, open-ended, substantially tubular member further comprises a selectively inflatable bladder.

13. The device of claim 1, wherein said flexible, open-ended, substantially tubular member further comprises a sealed bladder filled with a water-buoyant gas or liquid.

14. The device of claim 1, wherein said device is buoyant and thereby keeps said swimming goggles afloat when said swimming goggles are separated from a user and are in a body of water.

* * * * *